Figure 1A:
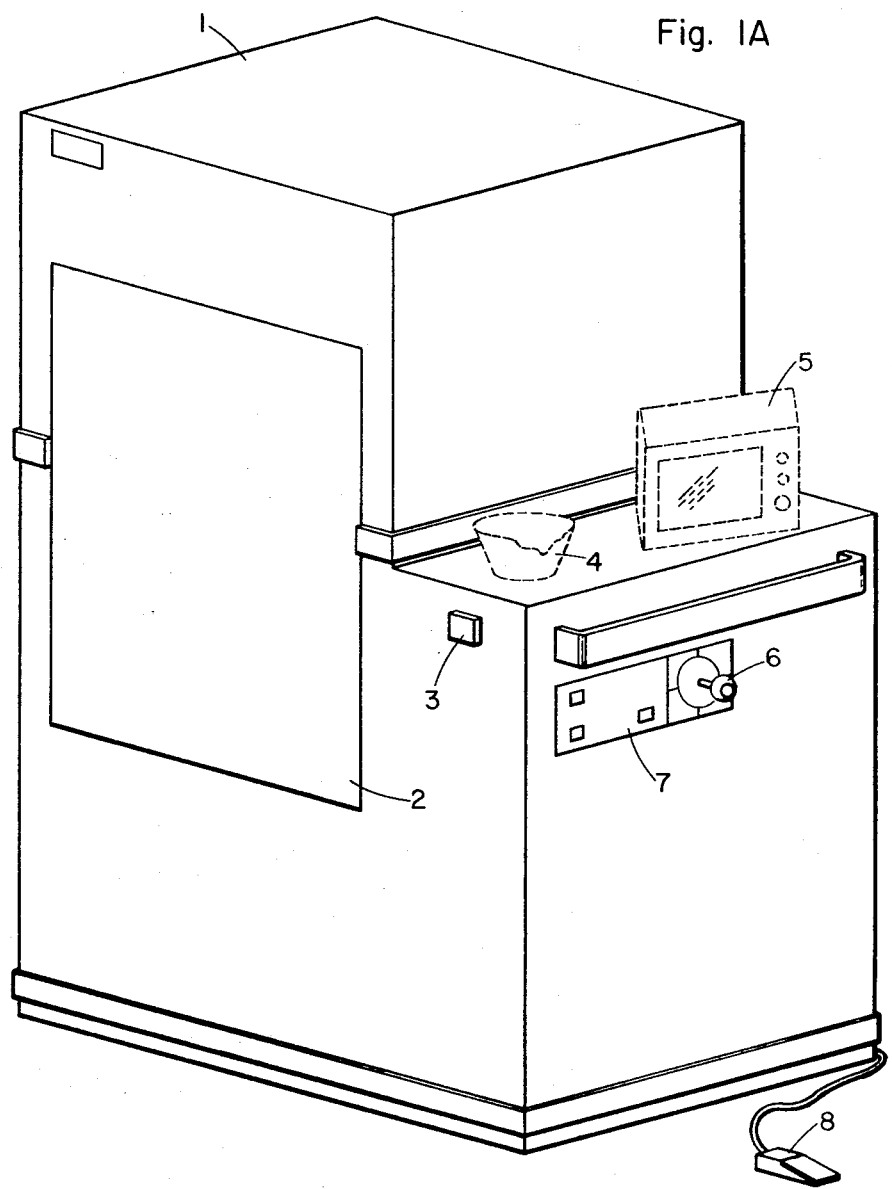

United States Patent [19]

Haas et al.

[11] Patent Number: 4,469,403
[45] Date of Patent: Sep. 4, 1984

[54] LENS SWITCHING SYSTEM FOR USE IN X-RAY INSPECTING DEVICES

[75] Inventors: David J. Haas, Suffern; Costas Blionas, New York; Joseph P. Muenzen, Pearl River, all of N.Y.

[73] Assignee: North American Philips Corporation, New York, N.Y.

[21] Appl. No.: 433,757

[22] Filed: Oct. 12, 1982

Related U.S. Application Data

[62] Division of Ser. No. 189,995, Sep. 23, 1980, Pat. No. 4,379,348.

[51] Int. Cl.$^3$ ............................................. G02B 7/14
[52] U.S. Cl. ................................................... 350/254
[58] Field of Search ............... 350/502, 254; 378/57, 378/62, 99, 189–192

[56] References Cited

U.S. PATENT DOCUMENTS

| | | | |
|---|---|---|---|
| 2,103,525 | 12/1937 | Gallasch | 350/254 |
| 2,103,573 | 12/1937 | Wilkinson | 350/254 |
| 2,236,069 | 3/1941 | Robinton | 350/254 X |
| 2,812,687 | 11/1957 | Eitel, Jr. et al. | 378/190 |
| 4,143,938 | 3/1979 | Feinbloom | 350/502 |
| 4,210,811 | 7/1980 | Dennhoven et al. | 378/57 |

FOREIGN PATENT DOCUMENTS 220556  3/1959  Australia .............................. 350/254

*Primary Examiner*—F. L. Evans
*Attorney, Agent, or Firm*—Paul R. Miller

[57] ABSTRACT

A lens switching system is provided for use in X-ray examination devices. The lens system includes at least a full viewing lens for viewing the entire object and a magnification lens which can be switched into the optical axis and controlled to different positions for magnifying the object. The optical axis for the magnification lens can be moved by means of a control handle controlling the lens system so that magnified portions of the object can be observed through the magnification lens.

9 Claims, 9 Drawing Figures

LENS SWITCHING SYSTEM FOR USE IN X-RAY INSPECTING DEVICES

This is a division of application Ser. No. 189,995, filed Sept. 23, 1980. This application is a divisional application of U.S. Pat. No. 4,379,348, and the benefits of the parent are hereby claimed for this divisional.

The present invention is directed to a security X-ray system in which magnified images can be obtained of an object being examined in the system. Consequently, detailed searching and examination of various parts of an article being viewed in a security screening system can be provided in accordance with the present invention.

Prior art X-ray examination systems have involved continuously moving conveyor belt systems to pass articles through X-ray examination areas, such as are utilized in airports as seen in U.S. Pat. No. 3,980,889. In addition, the use of TV inspection in X-ray microscopes, as in U.S. Pat. Nos. 3,743,845 and 3,846,632 have provided for movement of an article in X-Y directions, as well as rotation about an axis perpendicular to one of the X or Y directions. While such devices enable the microscopic examination of opaque articles by X-rays, the ability to examine portions of an overall article in security systems is not provided.

The present invention enables the examination of magnified portions of articles in X-ray security systems. In this respect, an article undergoing overall X-ray security inspected can be inspected at respective portions which catch the attention of an examiner. Namely, suspicious portions of an overall article which come to the attention of an examiner can be viewed under magnification by the present invention. This can be done in both a direct viewing situation and in a television viewing system.

Moreover, the present invention enables the examination of articles without their movement on a conveying system. That is, the placing of the article in a container-like structure enables the X-ray examination of an article, and the subsequent detailed magnification of portions of the article. In this respect, articles of substantial size may be examined, such as might be commonly found in customs examinations and/or security or prison systems.

The present invention involves a cabinet-type X-ray machine where all of the X-rays are contained within the cabinet. The unit is loaded through a large front door which makes the entire X-ray chamber accessible. The articles are loaded in any orientation into the X-ray chamber and the door is simply closed for subsequent X-ray examination. The X-ray chamber is oversized so that large items such as chairs, large suitcases, boxes, and etc. can be inserted into the system and be examined in different orientations with different viewing angles. The system has an ease of loading and unloading which is important for convenient operation of such systems.

With the article inserted into the X-ray chamber, the door is closed, and the article is exposed to X-rays in the chamber. In this respect, the source of X-rays provide a wide-beam exposure so that the article may be viewed through a fluorescent screen which converts the X-ray images into visible images. The visible images obtained from the fluorescent screen are reflected by two mirrors into an optical viewing system through which the image may be displayed in a television camera of directly viewed through a lens system.

The convenient aspects of the present invention involve a control system which enables switching from a full view of the fluorescent screen image to a magnified portion of the image. Further, a control knob permits the aiming of a lens at portions of the article, which appear suspicious, and the magnification of the image of such portions.

Consequently, the important aspect of the present invention includes the lens magnification switching system which selectively enables the viewing of the entire visible image of the fluorescent screen or only a magnified portion of the visible image. The lens magnification switching system involves at least two lenses, one of which provides magnification at least in the range from 3:1 to 10:1. This structure also includes an arrangement for moving the respective lenses into alignment with a viewing axis and the tilting of the magnification lens. By this arrangement, the overall viewed article in the X-ray chamber may be examined in magnified detail at those portions which appear to be important to an examiner.

Figure 1C:
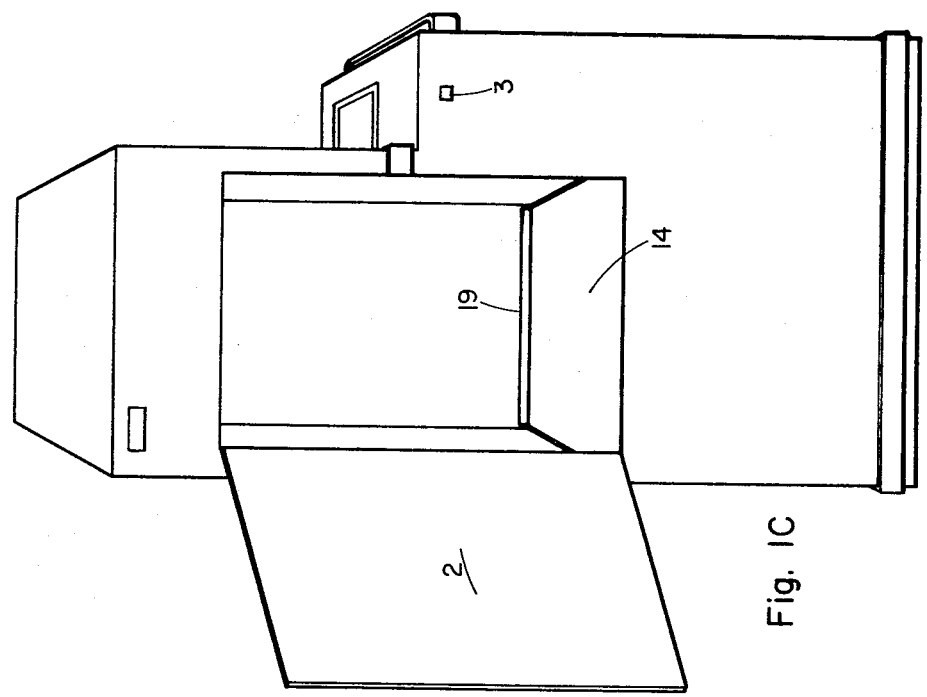
Figure 1B:
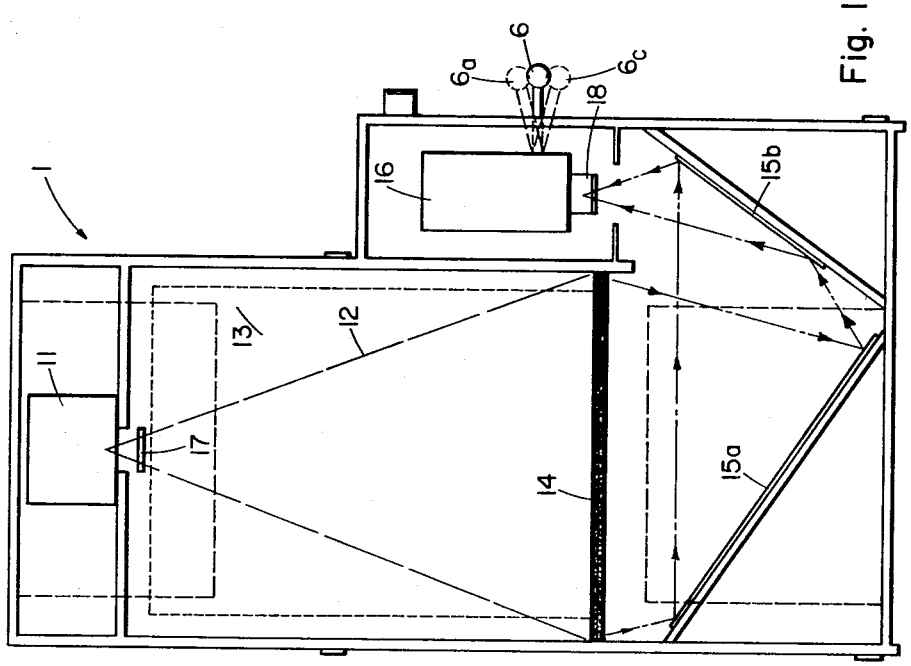
Figure 4:
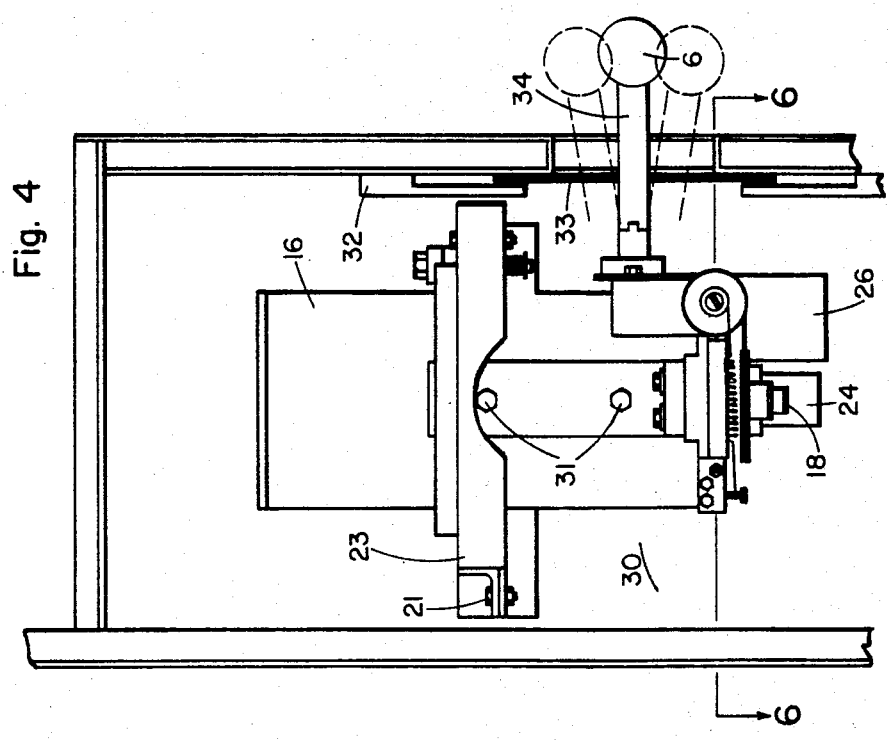
Figure 2A:
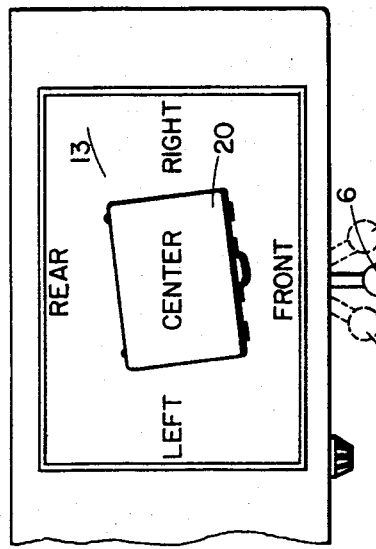
Figure 2B:
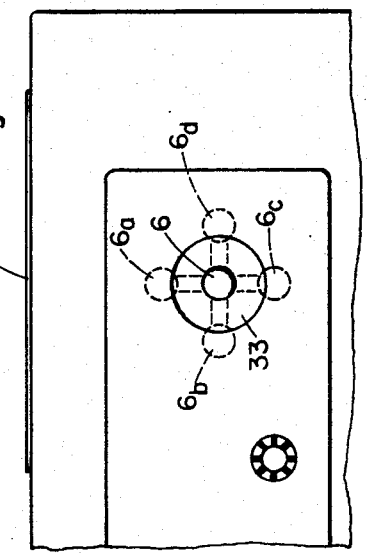
Figure 5:
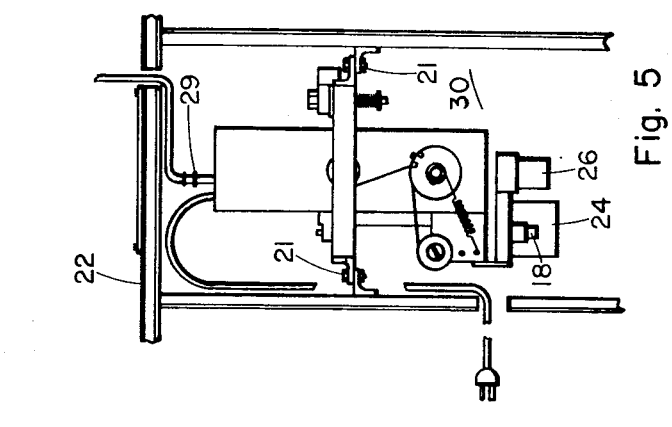
Figure 6:
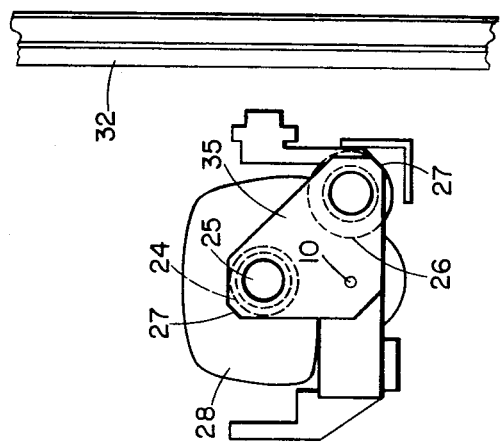
Figure 3:
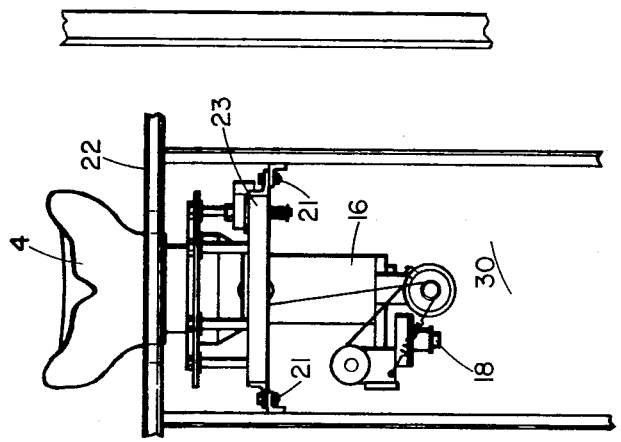

The details of this structure may be seen by reference to the drawing figures which show in detail the aspects of the present invention without limitation, and include FIG. 1A is an overall perspective view of the X-ray structure in accordance with the present invention, FIG. 1B schematically illustrates the X-ray and optical operation of the device, FIG. 1C shows the internal arrangement of the X-ray chamber in accordance with the present invention, FIG. 2A illustrates the placing of an article in the X-ray chamber and the consequent viewing thereof, FIG. 2B illustrates the potential motions of the control structure and its relation to the X-ray chamber, FIG. 3 illustrates the direct viewing system in accordance with the present invention, FIG. 4 illustrates the structure of the present invention which is used in TV controls, FIG. 5 illustrates a side-view of the arrangement in FIG. 4, and FIG. 6 illustrates a schematic sectional view through the lines VI—VI in FIG. 4.

The overall structure of the X-ray examination system is illustrated in FIG. 1A wherein the unit 1 includes a front loading door 2 of large size, such as approximately 2 feet by 4 feet. The unit 1 includes the control light 3 which indicates X-ray operation and control panel 7 includes the control knob 6 for variously selecting full view images of an article placed in the chamber or magnified portions of such articles. These X-ray images may be observed through the direct viewing arrangement 4 in the cabinet or the television structure 5 which may be attached to the cabinet.

The X-ray generator 11 illustrated in FIG. 1B may operate at high kilovoltage, such as 90 kV constant potential or may be continuously adjustable from a low to high kV, such as 50 to 90 kV at, for example, 0.5 mA tube current. The X-ray tube may include a beryllium window with a divergence angle as large as 45°. The X-ray beam cone 12 then diverges substantially in the X-ray chamber in order to cover the full dimensions of the lower portion of the X-ray chamber 13, particularly at the fluorescent screen 14 and any articles placed thereon. An X-ray filter 17 may also be utilized to modify the X-ray spectrum.

The bottom of the X-ray chamber 13 includes the fluorescent screen 14 which converts the X-ray images of articles placed in the chamber into visible images.

These visible images are reflected through a mirror system 15a and 15b into the optical system or arrangement 16 having an objective lens system 18.

As may be seen in FIG. 1C, the chamber into which articles are placed for X-ray examination is substantial in size. Consequently, everything from large suitcases through tables or chairs may be placed into the chamber for appropriate X-ray examination. The chamber 13 includes bumpers 19 around the lower edges to prevent damage to the wall of the X-ray chamber upon insertion of articles into the chamber.

In FIG. 2A the control knob 6 may be moved in a number of different positions to enable an examiner to view the front, the rear, the left side, or the right side of the chamber with the magnified optical system. The control function of this control knob 6 is in two parts. First, rotary motion of the control knob 6 changes the objective lenses between full field viewing and magnification, and secondly, lateral movement of the control knob 6 optically directs the magnification lens and its associated imaging arrangement to various portions of the fluorescent screen.

As may be seen in FIG. 2B the position of these movements of the control knob 6 may be seen respectively to arrive at the various portions of the viewing system. It may be noted that while the control knob 6 is shown with up 6a, down 6c, right 6d, or left 6b movement for viewing respective portions of the X-ray chamber, diagonal movements of the control knob 6 may occur so as to show the rear left of the chamber, for example, or any other portion of the chamber. These movements may represent: control knob up 6a, left screen view; control knob left 6b, front screen view; control knob down 6c, right screen view; and control knob right 6d, rear screen view. By this arrangement, any article, such as the luggage or baggage 20 in FIG. 2A may be examined thoroughly for illegal or contraband devices.

In FIG. 3 the direct viewing construction may be seen in which the viewing hood or eye shield 4 provides a direct view of the magnified portions of the article. In this arrangement, the movement of the control knob 6 effectively moves the entire optical system 16 by the pulley system 30 and pivots the swivel-type gimbel system 23. This gimbal system is mounted with the screws 21 to pivot gimballed portions so that a 5° to 10° side to side movement of the optical system may be made. The optical system 16 may consist of a light image intensifier with objective and binocular viewing lenses.

By this means, the lens system which is shown in partial view in FIG. 6 may be switched depending on whether the full fluorescent screen or entire article is to be viewed in the X-ray chamber, or a magnified portion thereof is to be viewed. Thus, the lens system 24 enables the full view of the device, while the lens system 26 enables magnified portions of the article to be viewed. The system normally provides the lens system 24 on the optical axis 25 of the optical system so that the full view or image of the article in the X-ray chamber 13 is seen. It is only through the manipulation of the control knob 6 that the magnification lens 26 is brought into position so that magnified portions of this article can be viewed. Such manipulation between the lens may occur by rotation of the control knob 6. Both the full field lens system 24 and the magnification lens system 26 pivot about an axis 10. The optical axis 25 is coincident with the pivot point 10 when both the direct viewing system 16 or the TV viewing system 16' are employed.

The construction of the present invention may be seen in more detail by reference to FIGS. 4–6 which relates to the television viewing system of the present invention. In this arrangement, a TV camera 16' is provided on the gimbal arrangement 23 to be moved by the control knob 6. This enables variously the switching of the lens system from the standard full field lens system 24 to the magnifying lens system 26, and also the control of the magnifying lens system 26 over portions of the article to be examined. Such movement is provided through the pulley system 30 by means of the control knob 6 and shaft 34.

The manipulation of the control knob 6 variously to bring either the magnifying lens system 26 or the full field lens system 24 into the optical system may proceed in accordance with the present invention to provide a magnified image of a portion of the article or a full image of the article. This may be viewed in the television structure 5 by way of the arrangement illustrated in FIGS 4 through 6. For example, the television camera 16' is connected to the television monitor 5 through the BNC connector 29 and resultant cable. As such, the viewing of the entire article by the full field lens system 24 occurs until manipulation of the magnification lens system 26 is provided with the control knob 6. The movement of the control knob 6 upwardly or downwardly, as well as in any direction in the plane of the system, as illustrated in FIG. 4, will bring the magnification lens system 26 into examination of the various portions of the article in the X-ray chamber. The opening through which the shaft 34 of the control knob 6 extends in the chamber may be closed by an X-ray impermeable material 33 having a hole therethrough for the extension of the shaft 34. This material may be moved within the brackets 32 so that the handle can be variously moved upward or downward or sideways without exposure of X-rays to an operator.

The arrangement of the present invention thus enables an operator to examine articles placed into the X-ray chamber 13. Upon closing the door 2 various safety interlock circuits are closed which prevent untimely exposure of persons to X-rays. Upon the closing of these interlock circuits, the ready light 3 comes-on to indicate the readiness of the unit to be used.

The operator may now turn on the X-rays through a switch on the control panel 7 or by standing on the foot pad 8 in FIG. 1A. With the direct viewing system the operator may view the object through the eye shield 4, and switch lenses by rotating the control knob 6. Then, the magnified image viewer may be aimed towards the portion of the fluorescent screen that is wished to be examined. By this arrangement the viewer will be able to see all portions of the fluorescent screen in the magnified mode.

Upon releasing the control knob 6 after such examinations, the magnifying lens system 26 moves back to its original position, and the full fluorescent screen viewing lens system 24 returns to a centered position along the optical axis. For examination of various articles in the system, the operator may vary the kV on the X-ray system over a range to improve the X-ray image contrast. The television system operates in substantially the same manner inasmuch as the entire fluorescent screen, or article, may be viewed in the television monitor 5, and magnified portions of the article may be found by manipulation of the control knob 6 to bring the magnifying lens system 26 into the optical axis. At the end of such examinations, as well as all examinations, a return of the lens system to view the full fluorescent screen may be provided by releasing the control knob.

The present application provides a mechanical linkage system which enables the manual movement of a gimbal holding a lens system in various directions, while at the same time enabling the lens system to be returned to the optical axis or center position automatically. This advantageously provides a full view of the fluorescent screen, for example upon turning the unit on, and simultaneously, the maintainance of the view in the center position of the fluorescent screen image upon rotation of the lens system to the magnified lens system 26.

With the use of the television camera and monitor, a dramatic advantage of universality is achieved. For example, any limitations as to operator height or size are eliminated.

The principal factor in terms of use of the present invention is that a zooming in and scanning about of the image of an object in the X-ray chamber can be achieved by way of a single control knob, and at the same time the operation can control the kV. That is, by a single handed arrangement, examination of the article can be achieved through the control knob 6, thus leaving a hand free for controlling the kilovoltage and performing any other desired function. Upon changing the X-ray kV, a more intense picture or more penetrating picture can be obtained.

In addition, a further advantage of the present invention can be that one learns faster and more easily how to direct the viewing systems by human factor design then if many controls or electrical switches had to be operated. The single control knob provides direct correlation between the control handle directions to the X-ray chamber contents.

The structure of the present invention enables the control knob 6 through its shaft 34 to be mechanically fastened to the gimbal 23, such as seen in FIG. 4 for example. By this manner, the gimbal moves according to wherever the control knob is physically positioned. Also, lens switching is accomplished by rotating the knob. This arrangement operates on a cable arrangement such that by simple gearing or pulley arrangements 30, the lenses may be rotated from one extreme to the other. Consequently, the lenses require no adjustments and the optical axis of any respective lens may be centered on the optical axis of the optical system. By this means, whether or not the full image position is utilized or the magnification portion is utilized, the arrangement is in optical use without any other manipulation.

In the arrangement of the optical magnification system, a lensing arrangement is provided to achieve a viewing dimension from approximately 3 by 3 inches to about 6 by 6 inches. This is achieved by magnification lenses having magnification ranging from around 3:1 to 10:1 since it has been found that higher magnifications may tend to lose orientation and position in the X-ray image.

What I claim:

1. A lens switching system for X-ray inspection arrangements comprising
    at least two lens systems, a first of said lens systems providing a full-field view of an object and the remaining said lens systems providing magnification of said object,
    a rotary plate holding said lens systems, said rotary plate being rotated about an axis parallel to an optical axis,
    first means for rotating said rotary plate about said axis to position a magnification lens system into alignment with said optical axis, and
    second means for maintaining said rotary plate with said full-field lens system in alignment with said optical axis except when said magnification lens system is used,
    wherein said first means includes a control handle operatively connected to said rotary plate for selectively moving said magnification lens system into alignment with said optical axis, said control handle controlling said magnification lens system for movement over portions of said object.

2. A lens switching system according to claim 1, wherein said control handle is movable perpendicular to its longitudinal dimension to move said magnification lens system for viewing said portions of said object, and wherein said control handle is rotatable about said longitudinal dimension to selectively bring said magnification lens system into alignment with said optical axis.

3. A lens switching system according to claim 2, wherein said second means automatically returns said full-field viewing lens system to alignment with said optical axis upon release of said control handle.

4. A lens switching system according to claim 1, wherein said control handle is mounted to a gimbal structure through said rotary plate for tilting said lens systems 5 to 10 degrees about said optical axis.

5. A lens switching system according to claim 2, wherein said magnification lens systems provide magnification ranging from 3:1 to 10:1.

6. A lens switching system according to claim 1, wherein said rotary plate is a flat plate.

7. A lens switching system according to claim 1, wherein direct viewing means are provided for viewing images of said object.

8. A lens switching system according to claim 1, wherein television viewing means are provided for viewing images of said object.

9. A lens switching system according to claim 1, wherein said magnification lens systems provide magnification ranging from 3:1 to 10:1.

* * * * *